United States Patent [19]

Hsu

[11] Patent Number: 5,070,010
[45] Date of Patent: Dec. 3, 1991

[54] METHOD FOR DETERMINING ANTI-VIRAL TRANSACTIVATING ACTIVITY

[75] Inventor: Ming Chu Hsu, New York, N.Y.

[73] Assignee: Hoffman-La Roche Inc., Nutley, N.J.

[21] Appl. No.: 428,555

[22] Filed: Oct. 30, 1989

[51] Int. Cl.$^5$ ............................................. C12Q 1/68
[52] U.S. Cl. ...................... 435/6; 435/69.1; 435/91; 435/172.3; 436/501; 536/27; 935/6; 935/10; 935/29; 935/36; 935/77; 935/78; 935/88
[58] Field of Search ................ 435/6, 91, 69.1, 172.3; 436/501; 536/27; 935/6, 10, 29, 36, 77, 78, 88

[56] References Cited

U.S. PATENT DOCUMENTS 4,738,922  4/1988  Haseltine et al. ...................... 435/68
4,981,790  1/1991  Haseltine et al. ................... 435/69.1

OTHER PUBLICATIONS

Berger et al. (1988) Gene, vol. 66; pp. 1–10.
Mavromara-Nazos, Virology 149:152–164 (1986).
Gelman et al., Proc. Natl. Acad. Sci., U.S.A. 82:5265–5269 (1985).
Colgrove et al., J. Virology (Sep. 1989) 4019–4026.
Cullen, Methods in Enzymology, 152:684–705 (1987).
Hedenskog et al., J. Medical Virology 19:325–334 (1986).
Sodroski et al., Science 229:74–77 (1985).
Arya et al., Science 229:69–73 (1985).
Gillespie, Molecular and Cellular Probes 3:73–86 (1989).

*Primary Examiner*—Robert A. Wax
*Assistant Examiner*—Ardin H. Marschel
*Attorney, Agent, or Firm*—George M. Gould; William H. Epstein; Patricia S. Rocha

[57] ABSTRACT

The anti-viral transactivating activity of a test substance is determined by (a) putting both the expression of the Secreted Alkaline Phosphatase gene and the viral transactivator gene under the control of a viral promoter responsive to the action of the transactivator, (b) transfecting cultured mammalian cells with plasmids which contain the gene constructs of (a) and cause cellular production of the transactivating factor and Secreted Alkaline Phosphatase (c) adding the substance to be tested, and (d) determining the amount of Secreted Alkaline Phosphatase produced, whereby inhibition of Secreted Alkaline Phosphatase production correlates with anti-viral transactivating activity.

15 Claims, 8 Drawing Sheets

FIG. 1A

"test plate"

FIG. 1B

"drug plate"

8ul Cmpd/ 8ul Cmpd/   repeat for other cmpds/broths,
Broth A   Broth B      each in duplicate

FIG. 1C

Similarly, repeat for the lower half of the plate

"drug plate"

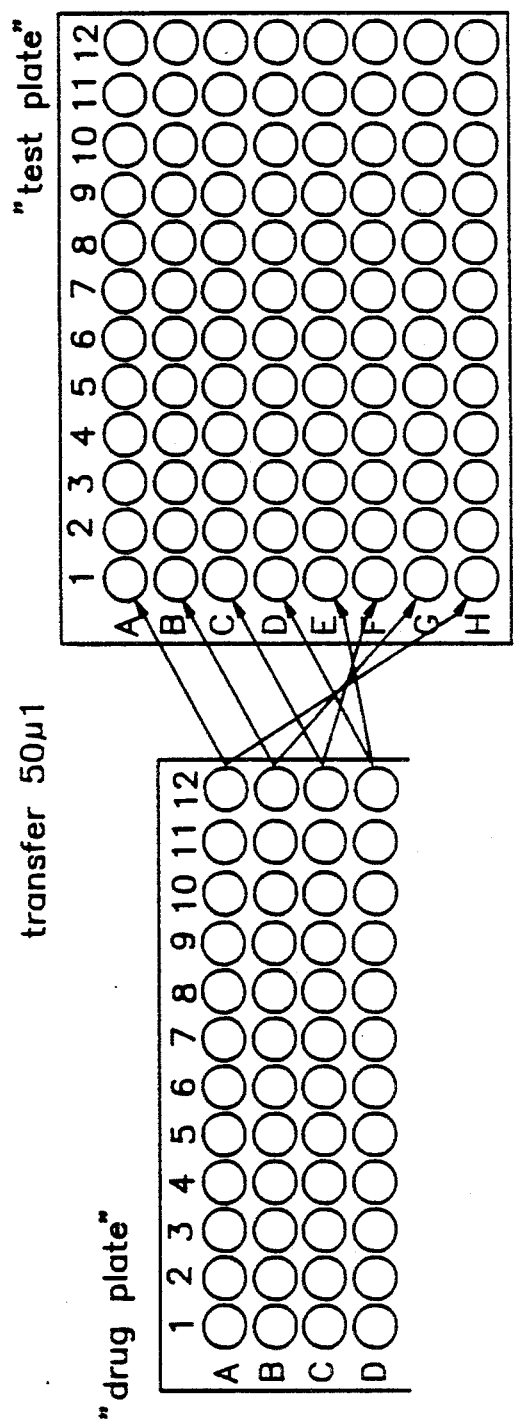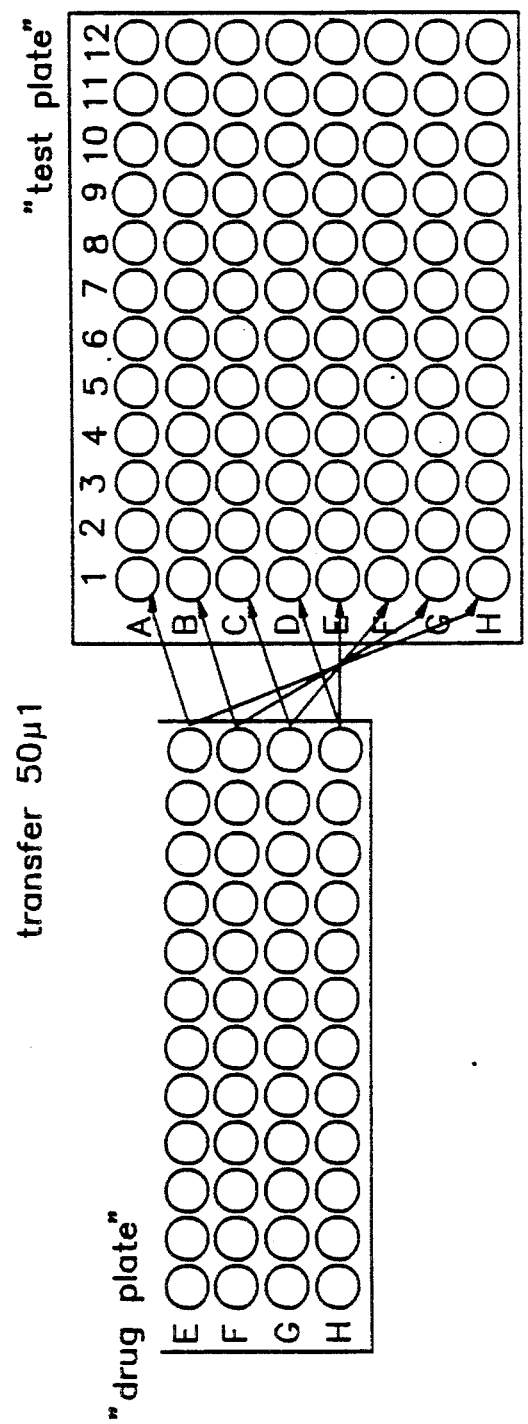

FIG. 7

PLAP          5'  CGGGCACCCGGGGGTCCGTGGTCCCCG  3'
Oligonucleotide  3'  GCCGTGGGCCCAATTGGGCACCAGGGC  5'

METHOD FOR DETERMINING ANTI-VIRAL TRANSACTIVATING ACTIVITY

TECHNICAL FIELD

The invention is directed to a method for determining the anti-viral transactivating activity of agents via a novel screening assay.

BACKGROUND OF THE INVENTION

Viral transactivator genes generally encode transactivating factors or proteins which activate the expression of genes under the control of promoters which repond to the actions of the transactivation. This activation promotes viral replication. Viruses such as HTLV-III (HIV), Hepatitis B virus, and Herpes Simplex Virus have transactivator genes encoding transactivating factors which in trans promote viral replication. The viral transactivator for of HIV is known as TAT, the viral transactivator of Hepatitis B Virus is the X gene product and the viral transactivator for Herpes Simplex is designated ICP4. Chemical compounds or biological materials which interfere with the activity of transactivating factors are good candidates for antiviral therapeutics.

For example, the development of drugs to treat AIDS involves screening vast numbers of agents for anti-HIV activity. Anti-HIV activity in turn can be assessed by a variety of parameters.

For example, it is known that HIV requires several viral proteins for effective viral replication that include but are not limited to reverse transcriptase (RT), protease, transactivating protein (TAT), and REV protein. The switch from viral latency to active replication requires the regulatory gene products TAT and REV. TAT protein transactivates the HIV-LTR promoter and amplifies viral replication many thousand fold. The TAT- responsive sequence has been mapped within the LTR sequence. The REV gene product is involved in the transport of viral messenger RNAs from nuclei to cytoplasm and is required for the production of viral structural proteins coded for by GAG, POL, and ENV genes. When the REV gene is impaired the infected cells do not make the viral structural proteins and no mature virions are produced. An agent which inhibits TAT would be expected to arrest HIV in the latent stage and can therefore be used therapeutically for patients infected with HIV including AIDS and ARC patients as well as for asymptomatic carriers. Thus it is important to have screening assays which can effectively detect the anti-TAT activity of chemical compounds.

The Hepatitis B virus (HBV) X gene product transactivates the viral promoters and is required for the virus to propagate in animal hosts. [See Colgrove et al., *J. Virol.*, 63: 4019 (1989)]. HBV causes persistent infections of liver cells that predispose hosts to liver cancer. An X gene inhibitor would suppress viral replication and thereby reduce the risk of liver cancer. The responsiveness of HBV promotors to X gene products has been demonstrated with heterologous gene constructs in laboratory tissue culture cell lines. [Colgrove, et al, *J. Virol.* 63: 4019 (1989)].

The Herpes Simplex virus (HSV) gene expression is coordinately regulated. The early and late genes (also called β and γ genes respectively) expression depend on the expression of the immediate early gene (also called α gene) expression. In particular the immediate early protein ICP4 transactivates the early and late gene promoters and is required for productive infection. [Maromara-Nazo et al., *Virology* 149: 152 (1986) and Gelman et al., *P.N.A.S.* 82: 5265 (1985)]. An inhibitor of ICP4 would block the reactivation of latent virus and would thereby have potential therapeutic applicability.

Screening assays which detect the anti-viral transactivating activity of various agents would be very useful in aiding the isolation of agents useful to treat various diseases.

SUMMARY OF THE INVENTION

The invention is directed to a method for determining the anti-viral transactivating activity of a test substance comprising:

a) contacting the test substances with a cultured first mammalian cell capable of expressing secreted Alkaline Phosphatase ("SeAP"), said cell comprising a gene capable of causing the expression of SeAP by said cell, a viral transactivator-activated promoter for activating said gene which causes SeAP expression by said cell and a transactivator gene which is capable of causing the expression of a viral transactivator which activates said promoter, to determine if said substance inhibits the production of SeAP by said cell;

b) contacting said substance with another cultured mammalian cell capable of expression SeAP, said cell comprising a gene capable of causing the expression of SeAP by said cell and a self-activating viral promoter which activates said SeAP expression to determine if said substance inhibits the production of SeAP by said second cell; and c) determining if the addition of the substance selectively inhibits the amount of SeAP produced by said first mammalian cell whereby such selective inhibition of SeAP expression by said first cell correlates to selective inhibition of virral transactivator expression and thereby demonstrates the anti-viral transactivating activity of the substance.

DESCRIPTION OF DRAWINGS

FIG. 1–3: Describe the assay plate configuration used to conduct the assay of the invention.

FIG. 7: provides the nucleotide sequence of bases 1510–1539 of the human placental alkaline phosphatase gene and of an oligodeoxynucleotide used to mutate the gene. The five mutated bases are shown underlined.

DETAILED DESCRIPTION

Figure 2A:
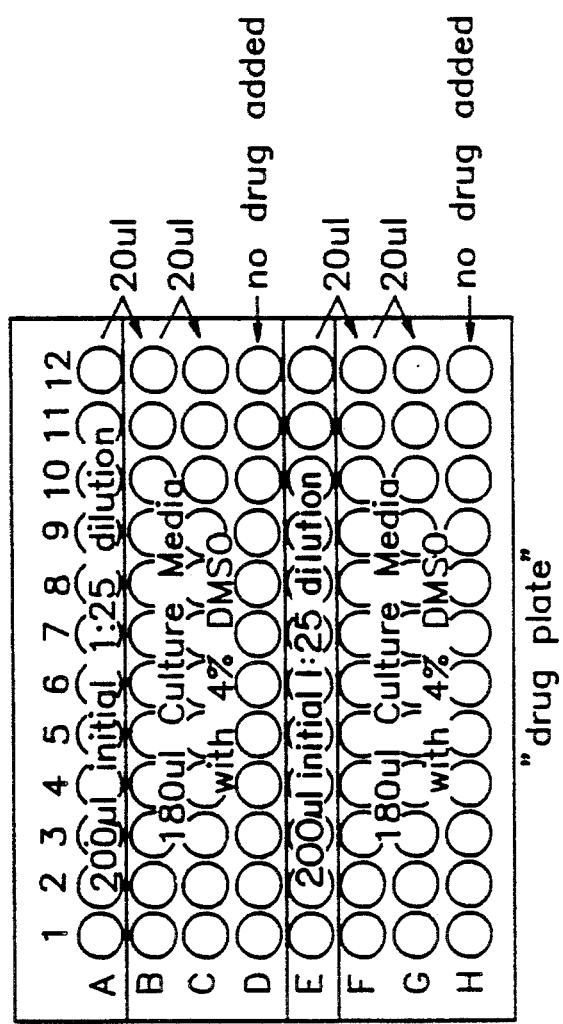

The preferred embodiment of the invention is directed to a method for determining the anti-TAT activity of an agent comprising transfecting cultured mammalian cells which causes cellular production of TAT and SeAP, adding the agent to be tested, and determining the amount of SeAP produced. The inhibition of SeAP positively correlates with anti-TAT activity. The greater the ability of an agent to inhibit SeAP, the greater is its anti-TAT activity.

The anti-TAT assay of the invention is based upon a transfection protocol wherein cultured mammalian cells are transfected with plasmids which case cellular production of TAT and SeAP. The cells may be transfected with one plasmid containing both the SeAP and TAT genes under the control of the Human Immunodeficiency Virus-Long Terminal Repeat (IV-LTR) promoter. However, in the preferred embodiment of the invention co-transfection with two plasmids is used. One plasmid carries the nucleotide sequence coding for SeAP under the control of the HIV-LTR promoter. The SeAP gene and plasmid construct are described in U.S. Pat. application Ser. No. 154,766 filed Feb. 11, 1988 and the corresponding foreign equivalents which have been published [Gene, 66:1 (1988)], which can be summarized as follows.

METHODS AND REAGENTS

Small scale isolation of plasmid DNA from saturated overnight cultures was carried out according to the procedure of Birnboim et al., Nucleic Acids Res. 7:1513 (1979). This procedure allows the isolation of a small quantity of DNA from a bacterial culture for analytical purposes. Unless otherwise indicated, larger quantities of plasmid DNA were prepared as described by Clewell et al., J. Bacteriol. 110:1135 (1972).

Specific restriction enzyme fragments derived by the cleavage of plasmid DNA were isolated by preparative electrophoresis in 1% GTG agarose (Seaplaque, FMC Inc. Rockland, ME). Fave×7.5 cm gels were run at 50 mA for 1-2 hours in Tris-Borate buffer (Maniatis et al., supra, p. 454) and then stained with 1 $\mu$g/ml ethidium bromide to visualize the DNA. Appropriate gel sections were excised and placed in a dialysis bag containing 500 $\mu$l of Tris-Borate buffer. The DNA was electroeluted into the Tris-Borate buffer, extracted twice with phenol and three times with chloroform and precipitated at $-20°$ C. with ethanol in the presence of 10 $\mu$g of tRNA carrier (yeast, Bethesda Research Laboratories, Gaithersburg, MD).

The restriction enzymes, DNA polymerase I (Klenow fragment) and T4 DNA ligase (T4 DNA polymerase) were products of New England Biolabs, Beverly, MA, and the methods and conditions for the use of these enzymes were from the manufacturer's protocol.

For the restriction endonucleases, a unit of activity is defined as the amount of enzyme needed to produce a complete digest of 1.0 $\mu$g DNA in 60 minutes in a total reaction volume of 0.05 ml, with digestion carried out at 37° C. The buffer used for all of these enzymes (restriction enzyme buffer) consisted of 100 mM NaCl, 10 mM Tris-HCl (pH 7.5), 5 mM $MgCl_2$ and 1 mM 2-mercaptoethanol.

T4 DNA ligation was carried out for 16 hours at 4° C. in ligation buffer containing 60 mM Tris-HCl (pH 7.5), 10 nM $MgCl_2$, 10 mM dithiothreitol and 0.1 mM ATP. A unit of T4 DNA ligase activity is defined as the amount required to give 50% ligation of HindIII fragments of lambda DNA in 30 minutes at 16° C. in 20 $\mu$l of incubation mixture and a 5' DNA termini concentration of 0.12 $\mu$M (300 $\mu$g/ml).

Klenow blunt-ending of single-stranded DNA ends was carried out in restriction enzyme buffer which had been adjusted to contain 1 mM of each of dGTP, dATP dCTP and dTTP. A unit of activity is defined as the amount converting 10 nmoles of deoxyribonucleotides to an acid insoluble form in 30 at 37° C.

Culture media used included Iscove's Modified Dublecco's Medium (IMDM) from Grand Island Biological Co. (GIBCO), Grand Island, NY, and Luria Broth (LB), containing 5 g Bacto-yeast extract, 10 g Bacto-tryptone (both products of DIFCO) and 10 g NaCl per liter, adjusted to pH 7.5. The antibiotic ampicillin was added to a final concentration of 50 $\mu$g/ml where indicated.

*Escherichia coli* strains were prepared for transformation by the calcium chloride procedure (Maniatis et al., supra, p. 254). The cells were transformed by the method of Dagert and Ehrlich [Gene 6:23 (1979)].

A 200 $\mu$l sample of competent cells suspended in 50 mM $CaCl_2$, 20% glycerol was combined with 100 $\mu$l of plasmid sample containing between 50 and 1000 ng of DNA in 10 mM $CaCl_2$. The mixture was kept on ice for 30 minutes and then heated at 42° C. for 2 minutes. One ml of LB was added and the mixture was incubated at 37° C. for 1 hour. The cells were plated on 37° C. LB agar plates with ampicillin and incubated for 16 hours at 37° C. to select for transformants.

COS cells were transfected using methods described by Butnick et al. [Mol. Cell. Biol. 5:3009 (1985)]. Ten-cm tissue culture dishes were seeded with $3 \times 10^6$ COS cells in 10 ml of IMDM supplemented with 10% fetal calf serum (FCS). 1% fungizone and 50 $\mu$g/ml gentamycin and incubated overnight in a 37° C., 5% $CO_2$ humidified incubator. The cells were washed once with 37° C. phosphate buffered saline (PBS), and 2 ml of 37° C. PBS containing 1 mg/ml of DEAE-dextran (Pharmacia) and the DNA to be transfected were added to the cells. The COS cells were then incubated and gently shaken at 5-minute intervals over a 30 minute period.

After this incubation, 20 ml of IMEM containing 10% FCS, 2% fungizone, 50 $\mu$g/ml gentamycin and 100 $\mu$M chloroquin were added to each dish. After 2½ hours of further incubation, the medium was replaced with fresh IMEM medium with 10% FCS, 1% fungizone, 50 $\mu$g/ml gentamycin and 10% dimethylsulfoxide for 2.5 minutes. This medium was then replaced with IMDM containing 10% FCS, 1% fungizone and 50 $\mu$g/ml gentamycin, the cultures were incubated at 37° C. for 72 hours, and the cells and media were then analyzed as described below.

*E. coli* strain MC1061 is available from the ATCC under accession No. ATCC 53338. this strain has been described by Casadaban et al. [J. Mol. Bio. 138:179 (1980)].

The COS cell line is available from the ATCC under accession No. CRL 1651. This cell line has been described by Gluzman et al. [Cell 23,:175 (1981)].

Primer-directed site-specific mutagenesis was performed according to the methods described by Morinaga et al. [Biotechnology 2:636 (1984)]. The synthetic oligonucleotide used to carry out the mutagenesis procedure was prepared by the phosphoramidite solid support method of Matteucci et al. [J. Am. Chem. Soc. 103:3185 (1981)].

Colony hybridization was performed using a method described by Maniatis et al., supra, p. 312. The same oligonucleotide used for primer-directed mutagenesis was used as probe for the hybridizations after 5' end labeling with γ-[$^{32}$P]-ATP using polynucleotide kinase according to the procedure of Maniatis et al., supra, p. 396. The labeling of larger DNA probes used to locate the PLAP gene was carried out using a random priming kit (International Biotechnologies, Inc.) according to the manufacturer's instructions.

Enzymatic activity of SEAP was determined as described by McComb et al., supra, with p-nitrophenyl phosphate as substrate. The incubation mixture was made 10 mM in L-homoarginine and heated for 10 minutes at 37° C. prior to assay, to inhibit endogenous phosphatase activity. One unit of alkaline phosphatase activity corresponds to 1μmol of substrate hydrolyzed per minute at 37° C.

One 10 cm plate of COS cells was set up and transfected as described above. Sixty hours post transfection, an aliquot of medium was transferred a 1.5 ml Eppendorf tube. The medium was clarified by centrifugation for 2 minutes at 4° C. at top speed. The clarified medium was removed to another Eppendorf tube and heated at 65° C. for 5 minutes. The medium was centrifuged for 2 minutes at 25° C. at top speed. The medium was removed to a new Eppendorf tube and kept at 4° C. The medium samples were assayed in two ways.

In the first assay, 10 μl of medium, 80 μl of alkaline phosphatase (AP) buffer (1.0 M Diethanolamine-HCl, pH 9.8, 0.5 mM MgCl$_2$, 20 μM ZnSO$_4$) and 10 μl of 100 mM L-homoarginine were preincubated for 10 minutes at 37° C. in a 96-well flat bottom cell culture plate (Corning). Twenty μl of 60 mM p-nitrophenylphosphate in AP assay buffer prewarmed to 37° C. were then added to the above mixture. The OD$_{405}$ of the reaction mixture was read in an Artek automatic vertical beam plate reader.

In the second assay, 100 μl of medium, 200 μof 1.3×AP assay buffer and 30 μl of 100 mM L-homoarginine were preincubated at 37° C. Twenty μl of 174 mM p-nitrophenyl phosphate in 1.3×AP assay buffer prewarmed to 37° C. were added, and the enzyme reaction was followed as above. The heating step and the inclusion of L-homoarginine in the assay mixture were performed to inhibit endogenous phosphatase activities.

PREPARATION OF HUMAN PLACENTAL ALKALINE PHOSPHATASE cDNA

A λgt10 library consisting of about 500,000 independent recombinant plaques was constructed according to the method of Huynh et al, in DNA Cloning: A Practical Approach, 1985, Glover, ed., IRL, Arlington, VA, Vol. 1, pp. 49-78, which is hereby incorporated by reference. The cDNA used was derived from placental polyadenylated mRNA, isolated from a single term placenta obtained from Mountainside Hospital, Montclair, NJ. The cDNA was prepared in vitro by the method of Gubler et al., Gene 25:263 (1983), hereby incorporated by reference, and about 10 ng were used for construction of the library.

Screening was carried out by the tetramethylammonium chloride method [Wood et al., Proc. Natl. Acad. Sci. USA 82:1585 (1985)], using two oligodeoxyribonucleotides encompassing nucleotide regions 600-624 an d1495-1521 of the published sequence of human placental alkaline phosphatase (PLAP). The nucleotide sequence of one PLAP allele has been disclosed by Kam et al., Proc. Natl. Acad. Sci. USA 82:8715 (1985).

Four independent clones ere obtained, two of which contained a full-length insert for PLAP. Seventy-five percent of one of the inserts, designated PLAP 2.4, was sequenced by the method of Sanger et al., Proc. Natl. Acad. Sci. USA 74:5463 (1977), using a BRL gel sequencing system. This insert proved to be identical to the allele reported by Millan, J. Bio. Chem. 261:3112 (1986).

CONSTRUCTION OF PLASMID pBC12/PLAP, ENCODING COMPLETE HUMAN PLACENTAL ALKALINE PHOSPHATASE

Insert PLAP 2.4 was excised from its clone using EcoRI and then blunt-ended with Klenow DNA polymerase I. The result was a blunt-ended 2.3 kilobase (kb) cDNA fragment containing the entire translated region and 0.7 kb of a 3'-untranslated region of human PLAP [Berger et al., Proc. Natl. Acad. Sci. USA 84:695 (1987)].

To construct plasmid pBC12/PLAP, the 2.3 kb fragment was inserted into plasmid pBC12BI as described by Berger et al., Proc. Natl. Acad. Sci. USA 84:4885 (1987). Plasmid pBC12IB is a eukaryotic expression vector containing bacterial origin of replication, a β-lactamase (ampicillin resistance, amp$^R$) gene, simian virus 40 origin of replication, the Rous sarcoma virus long terminal repeat transcription control region, and the genomic rat preproinsulin gene. The latter contributes an intron and an efficient polyadenylation signal.

The expression vector pBC12BI has been described [Cullen, Methods in Enzymology 152:684 (1987)] and differs from the available starting vector pBC12MI only in that pBC12BI lacks a 74 base pair BstNI to HindIII fragment which was excised from the Rous Sarcoma Virus long terminal repeat present in pBC12MI. The absence of presence of this sequence has no effect on the utility of this promoter or vector. Plasmid pBC12BI in E. coli strain RR1 has been deposited with the American Type Culture Collection and assigned accession No. ATCC 67617.

Plasmid pBC12/PLAP was use to construct the final exemplary expression vectors of this invention in several steps. First, a segment of the expression vector pBC12/PLAP was deleted. Secondly, the PLAP gene was mutated to encode a secreted form of the enzyme. Finally, the mutated gene was altered at both termini, so that it could be readily inserted into appropriately prepared expression vectors.

CONSTRUCTION OF SECRETED HUMAN PLACENTAL ALKALINE PHOSPHATASE EXPRESSION VECTOR pBC12/PLAPΔ489

PLAPΔ489 is the human placental alkaline phosphatase lacking the 24 carboxyl-terminal amino acid residues of the wild-type enzyme. This mutant was produced by placing a stop codon in the wild type PLAP gene after amino acid residue 489, by the site-directed mutagenesis method described above.

Before site-directed mutagenesis of the PLAP gene would be performed, a 700 nucleotide fragment of plasmid pBC12/PLAP was deleted by restriction endonuclease treatment with KpnI. Five μg of pBC12/PLAP was incubated with 48 units of enzyme for 3 hours at 37° C. The reaction mixture was then run in a 0.9% agarose gel, and the cut vector was isolated as described above. One-hundred-fifty ng of this vector was incubated with T4 DNA ligase for 16 hours at 4°, and the reaction mixture was used to transform E. coli strain MC1061 cells.

Transformants were selected for ampicillin resistance. Plasmid DNA was obtained by performing minilysates of several colonies and analyzing by KpnI cleavage followed by electrophoresis through a 1% agarose gel. A large scale plasmid preparation was made from cells containing the vector lacking the 700 nucleotide KpnI fragment. This plasmid was designated pBC12/PLAPΔKPN.

To carry out site-directed mutagenesis of pBC12/PLAPΔKPN, a 29-mer deoxyoligonucleotide primer was prepared by the phosphoramidite solid support method as described above. The sequence of this 29-mer primer and that of the region of the DNA to be mutated are shown in FIG. 7. The 29-mer primer contained 12 deoxynucleotides complementary to the bases on each side of the region to be mutated on one of the DNA strands. Mutation of the wild type gene to the 5 non-complementary nucleotides contained in the 29-mer primer (shown underlined in FIG. 7) created a stop codon after the nucleotides encoding amino acid residue 489 and a novel HpaI site in the resulting vector.

Twenty picomoles of the 29-mer primer were phosphorylated with 10 units of polynucleotide kinase (New England Biolabs) by incubating for 2 hours at 15° C. in buffer containing 70 mM Tris-HCl, pH 7.6, 10 mM $MgCl_2$, 5 mM dithiothreitol and 100 mM ATP. One unit of activity is defined as the amount of enzyme catalyzing the production of one nmole of acid-insoluble $^{32}P$ in 30 minutes at 37° C.

To carry out the mutagenesis procedure, 20 μg of pBC12/PLAPΔKPN were incubated with 36 units of BssHII and 84 units of KpnI in buffer containing 25 mM Tris-HCl, pH 7.8, 10 mM $MgCl_2$, 100 μg/ml bovine serum albumin and 2 mM β-mercaptoethanol for 24 hours at 37° C. The largest vector fragment produced, called the "gapped vector", was isolated in a 1% preparative agarose gel. Twenty μg of pB12/PLAPΔKPN were linearized with 20 units of PvuI by incubating at 37° C. for 16 hours, extracted with phenol/chloroform, precipitated in ethanol and taken up in water.

Equal 100 ng quantities of the linearized and gapped plasmids were mixed with a 20-fold molar excess of the phosphorylated oligonucleotide in 10 μl of water, and 2 μl of 10×Klenow buffer [1 M NaCl, 65 mM Tris-HCl (pH 7.4), 45 mM $MgCl_2$ and 10 mM 2-mercaptoethanol] were added. The mixture was treated for successive periods of 5, 30, 30 and 5 minutes at 100° C., room temperature, 4° C. and on ice, respectively, after which the sample was brought to a volume of 20 μl by the addition of 2 μl of 10 mM ATP, 4 μl of a mixture of 2.5 mM each of dCTP, dATP, dGTP and TTP, 0.5 μl of Klenow polymerase I (2.5 units of activity) and 1 μl of T4 DNA ligase (0.8 units of activity).

The mixture was incubated for 16 hours at 15° C. and then used directly to transform E. coli strain MC1061. Transformants were selected on LB agarose plates with ampicillin, and colonies from the plates were lifted onto nitrocellulose filters and screened for the presence of a sequence homologous to the 29-mer primer used in the mutagenesis procedure, using the synthetic oligonucleotide kinase labeled with γ-[$^{32}P$]-ATP as a probe.

Positive colonies were further screened by the method of Birnboim et al. for the presence of an expected HpaI restriction site. Because colonies obtained by this procedure are mixed (Morinaga et al., supra), a positive DNA sample was used to retransform E. coli MC1061, and resulting colonies were rescreened for the HpaI restriction site. A positive colony thus identified, which was designated pBC12/PLAPΔ489, was identical to pBC12/PLAPΔKPN but for the 5 mutated nucleotides.

CONSTRUCTION OF FINAL EXPRESSION VECTORS pBC12/RSV/SEAP (ALSO REFERRED TO AS pRSV/SeAP) AND pBC12/HIV/SEAP (ALSO REFERRED TO AS pHIV/SeAP)

The preparation of the final expression vectors was carried out in stages, entailing in succession (1) preparation of the vectors into which a modified human alkaline phosphatase gene could be inserted, (2) modification of the human alkaline phosphatase gene to obtain a movable human alkaline phosphatase gene fragment, and (3) insertion of this fragment into the prepared vectors.

One of the plasmids used for these constructions was pBC12BI, described above. The other was pBC12/HIV/IL-2 [Cullen, Cell 46:973 (1986)]. Plasmid pBC12/HIV/IL-2 was prepared by excising the Rous Sarcoma Virus Long Terminal Repeat from the available vector pBC12/RSV/IL-2 by cleavage with NcoI and HindIII. Subsequently, a Human Immunodeficiency Virus (HIV) Long Terminal Repeat (LTR) XhoI to HindIII DNA fragment was inserted using standard techniques. Plasmid pBC12/HIV/IL-2 in E. coli strain RR1 has been deposited with the American Type Culture Collection and assigned accession No. ATCC 67618.

To construct the final exemplary expression vectors of this invention, 5 μg of plasmid pBC12BI or pBC12/HIV/IL-2 DNA were treated with 20 units of BamHI in 50 μl of restriction enzyme buffer for 2 hours at 37° C. The reaction mixture was then blunt-ended by Klenow fragment treatment with 5 units of enzyme for 20 minutes at 25° C., after which the reaction was stopped by phenol extraction and ethanol precipitation.

One μg of blunt-ended pBC12BI or pBC12/HIV/IL-2 DNA was then incubated in 10 μl of ligation enzyme buffer together with 0.2 μg of phosphorylated XhoI linker DNA [d(pCCTCGAGG); New England Biolabs] and 1 unit of T4 DNA ligase at 15° C. for 15 hours.

The reaction was stopped by ethanol precipitation, and the XhoI linker concatamers created by the ligation reaction were trimmed by treatment with 60 units of XhoI in 100 μl of restriction enzyme buffer for 3 hours at 37° C. After an additional ethanol precipitation step, the pBC12BI or pBC12/HIV/IL2 DNA was incubated for self-ligation in 20 μl of ligation enzyme buffer in the presence of 1 unit of T4 DNA ligase at 15° C. for 15 hours. The ligation reaction mixture was then used directly to transform E. coli strain MC1061, and transformants were selected on LB agar with ampicillin.

The DNA obtained from ampicillin resistant colonies was screened by restriction endonuclease cleavage with XhoI, followed by analysis of the DNA fragments produced by electrophoresis in a 1% agarose gel containing 10 μg/ml ethidium bromide.

Plasmids derived from starting vector pBC12BI or pBC12/HIV/IL2, which had acquired a XhoI site, were thus prepared and identified. These plasmids were designated plasmid pBC12BI(+X) and plasmid pBC12/HIV/IL2(+X), respectively.

Plasmids pBC12BI(+X) and pBC12/HIV/IL2(+X) were then prepared in larger quantity by the lysis procedure of Birnboim et al. Final preparation of the cloning vectors was carried out by leaving 5 μg of pBC12BI(+X) or pBC12/HIV/IL2(+X) NDA with 20 units of HindIII and 20 units of XhoI, and isolating a 3.9 kb pBC12BI(+X) or 4.4 kb pBC12/HIV/J12(+X) vector fragment after electrophoresis through a 1% agarose gel.

Having thus prepared the vectors used to receive a modified human alkaline phosphatase gene, the modified gene was prepared using plasmid pBC12PLAPΔ489. To obtain a moveable human alkaline phosphate gene fragment for cloning into vectors pBC12BI(+X) and pBC/HIV/IL2(+X), unique restriction sites were created in pBC12/PLAPΔ489 at the 5' and 3' ends of the human alkaline phosphatase gene.

Five μg of plasmid pBC12/PLAPΔ489 DNA were treated with 20 units of ApaI in 50 μof restriction enzyme buffer for 2 hours at 37° C. After ethanol precipitation, the DNA was blunt-ended by T4 DNA polymerase with 1 unit of enzyme for 5 minutes at 37° C., after which the reaction was stopped by phenol treatment and another ethanol precipitation.

One μg of blunt-ended pBC12/PLAPΔ489 DNA was then incubated together with 0.2 μof HindIII linker DNA (phosphorylated 5'-GAAGCTTC-3', Boehringer-Mannheim) and 1 unit of T4 DNA ligase in 10 μl of ligation enzyme buffer at 15° C. for 15 hours. After stopping the ligation reaction by ethanol precipitation, the excess HindIII linker DNA ligated to pBC12/PLAP was removed by treatment with 60 units of HindIII in 100 μl of restriction enzyme buffer for 3 hours at 37° C.

After ethanol precipitation, the modified pBC12/PLAPΔ489 DNA was self-ligated in 20 μl of ligation reaction buffer with 1 unit of T4 DNA ligase at 15° C. for 15 hours. The ligation reaction mixture was used directly to transform E. coli strain MC1061, and transformants were selected in LB agar containing ampicillin. The plasmid DNA of ampicillin resistant colonies was screened by restriction endonuclease cleavage with HindIII and ApaI, followed by gel electrophoresis in 1% agarose. One plasmid which had lost the ApaI site and acquired a HindIII site was thus identified and designated plasmid pBC12/PLAP≠489(+H). A large-scale preparation of this plasmid was made as described above.

Five μg of plasmid pBC12/PLAPΔ829(+H) DNA were treated as noted with 20 units of KpnI and then blunt-ended by T4 DNA polymerase. To 1 μg of this DNA, 0.2 μg of XhoI linker DNA was ligated as described above. After transformation of E. coli strain MD1061 with the ligation mixture and screening of the plasmid DNA of ampicillin resistant colonies with the restriction endonucleases XhoI and KpnI, one plasmid which had lost the KpnI site and acquired a XhoI site was identified and designated pBC12/PLAP(+H,X).

After these manipulations, the human alkaline phosphatase gene was flanked by unique HindIII and XhoI restriction sites in plasmid pBC12/PLAPΔ489(+H,X). A large-scale plasmid preparation of pBC12/PLAPΔ489(+H,X) was performed as above.

Final preparation of the human alkaline phosphatase gene fragment was carried out by cleaving 5 μg of pBC12PLAPΔ489(+H,X) with 20 units each of HinDIII and XhoI. A 1.9 kb human alkaline phosphatase gene fragment was isolated after electrophoresis through a 1% agarose gel. This gene fragment was inserted into the above vectors as follows.

One hundred ng of the prepared vector fragments of pBC12BI(+X) or pBC12/HIV/IL2(+X) were mixed with 500 ng of the human alkaline phosphatase gene fragment in 20 μof ligation buffer and incubated with 1 unit of T4 DNA ligase at 15° C. for 15 hours.

The ligated DNA was then used to transform E. coli strain MC1061, and transformants were selected on LB agarose plates with ampicillin. The plasmid DNA of resistant colonies was screened by restriction endonuclease digestion with HindIII and XhoI, followed by 1% agarose gel electrophoresis. Two plasmids containing the appropriately modified human placental alkaline phosphatase gene thus prepared were identified and designated pBC12/RSV/SEAP [pRSV/SeAP] and pBC12/HIV/SEAP [pHIV/SeAP .

The cultured mammalian cells used for transfection are any suitable mammalian cells such as CV-1 monkey kidney cells, chicken embryo fibroblasts, Chinese Hamster ovary cells, HeLa cells, COS cells, etc. In the preferred embodiment of the invention cells from an African green monkey kidney cell line (COS cells) are used and they are transformed by SV40 and amplify plasmid carried the sequence of SV40 replication orgin such as pHIV/SeAP. The second plasmid contains the nucleotide sequence coding for TAT also under the control of the HIV-LTR promotor. nucleotide sequence of TAT is known The following plasmids are on deposit: pBC12Bl-ATCC #67617: pBC12/HIV/IL-2-ATCC #67618: and pBC12Ml-ATCC #67109. These plasmids are easily available starting materials for contructing the plasmids mentioned herein, which construction is also exemplified in U.S. Pat. Application Ser. No. 54,766.

It is important that the amount of TAT protein produced by the HIV-TAT plasmid in the cells is such as to produce sub-maximal amounts of SeAP, since TAT protein is a very potent activator of HIV-LTR-driven genes. If excessive amounts of TAT protein are produced it will be difficult or impossible to identify TAT inhibitors. The TAT level may be further controlled to produce a linear SeAP response by regulating the amount of TAT plasmid added. A further increase in the sensitivity of the assay is achieved by putting TAT gene under the control of HIV-LTR. The production of TAT is then self-regulated. In this assay an inhibitor of TAT protein action would prevent production of SeAP protein as well as blocking further production of TAT proteins. Such a linear relationship confers a great sensitivity to the assay and ensures an inhibitor of TAT function will reduce SeAP production.

Control cells for the assay are made by co-transfecting a second batch of mammalian cells with two plasmids. The first plasmid contains the HIV-LTR/TAT construct mentioned above, and the second plasmid contains the SeAP gene under the control of the Rous Sarcoma Virus/Long Terminal Repeat (RSV-LTR) promotor. The RSV-LTR/SeAP construct is described above. SeAP under the control of RSV-LTR is unresponsive to TAT. The control cell line serves as a negative control as well as an indicator of nonspecific cytotoxicity or direct inhibition of SeAP activity which a test compound may exhibit. The transfection procedure is as set forth in Cullen, *Methods in Enzymology*, 152: 684 (1987).

The transfected experimental and control cells will secrete SeAP into their culture media. The concentrations of SeAP in the supernatant media of the transfected test and control cells is assayed according to methods well known in the art, for example, colorimetric assays. The preferred method is a colorimetric assay as set forth in Example 5. The absorbance reading is taken after test compound is added to control and test cells for a given length of time e.g. 48 hours. Compounds suitable for assay are synthetic compounds as well as microbial broths and biological preparations such as peptides, microbial broth extracts, plant extracts, or other biological molecules.

Various dilutions of the test compound may be tested to determine the effective inhibitory ranges.

The invention is also directed to determining the anti-viral transactivating activity of agents against other viruses such as HBV and HSV.

Preferred also is a method for determining the anti-X transactivating protein activity of an agent comprising transfecting cultured mammalian cells with plasmids which cause cellular production of the trans-activating factor X and SeAP, adding the agent to be tested, and determining the amount of SeAP Produced. The inhibition of SeAP positively correlates with the anti-X activity of the agent. In this assay system the SeAP gene expression is most suitably put upstream from the gene sequence encoding the HBV core antigen. The promotor used should include the restriction DNA fragment from the unique XhOI, site to the FspI site as set forth in Colgrove mentioned previously. The expression of the X gene is then put under control of the same promoter. The X gene sequence used will include the restriction DNA fragment from the unique NcOI, site at the X gene initiation codon to the first downstream Bgl II site [Colgrove, supra]. The RSV/SeAP construct used in the anti-HIV TAT assay can be used as a negative control and a control for nonspecific cytotoxicity in this assay as well.

Also preferred is a method for determining the anti-ICP4 activity of an agent comprising transfecting cultured mammalian cells with plasmids which cause cellular production of ICP4 and SeAP, adding the agent to be tested, determining the amount of SeAP produced, whereby the inhibition of ICP4 positively correlates with the anti-ICP4 activity of the agent. For this assay configuration SeAP gene expression is put under the control of the HSV-TK gene Promotor. The TK gene is an early gene. The natural TK coding sequence is replaced by the SeAP gene coding sequence [Maromara-Nazo, et al., *Virology*. 149: 152 (1986) and Gelman, et al., *P.N.A.S.* 82: 5265 (1985)]. The gene which encodes ICP4 is put under the control of the TK promotor. The RSV/SeAP used in the anti-HIV TAT assay may be used as a negative control and a control for cytotoxicity.

The present invention will be further described in connection with the following Examples which are set forth for the purposes of illustration only.

EXAMPLE 1

Reagent Preparation

L-Broth: 10g bacto-tryptone, 10g yeast extract and 5g NaCl were added to a 1 liter flask. $H_2O$ was added to a final volume of 1 liter. The mixture was autoclaved, and stored at 4°. Before use, 50µg ampicillin/ml broth (10 mg/200 ml) was added. All the plasmids used in the assay carried the ampicillin resistance gene.

10X M9 salts: 60g $NaH_2PO_4$, 30g $KH_2PO_4$, 10g $NH_4Cl$, and 5 g NaCl were added to a 1 liter flask. $H_2O$ was added to a final volume of 1 liter. The mixture was autoclaved and stored at room temperature Supplemented M9 Medium: 200 ml 10X M9 salts, 40 ml 20% Glucose, 20 ml 0.1M $MgSO_4$, 20 ml 0.01M $CaCl_2$, (prepared and autoclaved separately) 2 ml 2 mg/ml thiamine (Vitamin $B_1$ —filter sterilized) and 1678 ml sterile $H_2O$ were mixed. 100 mg ampicillin and 800 mg uridine were added immediately prior to use.

Sucrose/Tris: 7.5 ml 1M TriS-HCl, pH 8, 37.5 g sucrose were mixed and $H_2O$ added to a final volume of 150 ml Lysozyme/Tris: 100 mg lysozyme was added to 7.5 ml 1M Tris-HCl and 22.5 ml $H_2O$.

Triton lysis buffer: 5.0 ml 1M Tris-HCl, pH 8, 12.5 ml 0.5M EDTA, pH 8, 0.4 ml Triton X-100 and 82.1 ml $H_2O$ were mixed.

1X SSC: 0.15M NaCl, 0.015M Na-citrate, pH 7.4

TE: 10 mM Tris-HCl, 1 mM EDTA, pH 8

RNase A: Stock solution of 10 mg/ml, was boiled for 10 min to inactivate any contaminating DNase, and stored at $-20°$ C.

Phenol: saturated with TE, pH 8 chloroform and chloroform with 1% iso-amyl alcohol

2M Na-acetate

100% Ethanol

Choramphenicol

CsCl

Ethidium Bromide: Stock solution was 2 mg/ml, stored at

4° C.

Light mineral oil

CsCl-saturated iso-amyl alcohol

EXAMPLE 2

Growing and pelleting *E. coli* transformed with plasmid 10 ml of L-Broth containing ampicillin was inoculated with a colony of *E. coli* transformed with the appropriate plasmid. The culture was grown overnight at 37° C.

Then 200 ml of L-Broth containing ampicillin was inoculated with the culture prepared above. The culture was grown overnight at 37° C. with shaking.

Supplemented M9 medium with ampicillin, 2 liters/flask, were prepared in each of five 4-liter flasks. Each flask was inoculated with 40 ml of the culture prepared in the previous step. The culture was shaken at 37° C. until the culture reached an O.D. of 0.8-1.0 at 590 nm (approximately 5 hours). At this point, 0.5 g chloramphenicol were added to each flask and shaking was continued at 37° C. for approximately 16 hours. The bacteria were pelleted in 500 ml bottles using a GS3 rotor in Sorvall Superspeed centrifuge spinning for 10 min at 8000 rpm. The supernatant was discarded.

EXAMPLE 3

Recovery and purification of plasmid DNA

The pellets were resuspended and pooled in a total volume of 120 ml freshly prepared, chilled Sucrose/-Tris in a 1-liter flask. 30 ml of freshly prepared lysozyme/Tris were added to the cells in the flask and mixed by swirling. The mixture was left on ice 5 minutes. 30 ml of 0.5 M EDTA, pH 8, were added and mixed by swirling. The mixture was left on ice for 5 min. 50 ml TRITON (Sigma Chemical Co.) Lysis buffer was added and with swirling and the mixture was left on ice for an additional 10 minutes. If the mixture did not become very viscous, it was incubated for another 5 min at 45° C. The mixture was carefully transferred into tubes for use in a Beckman 45Ti ultracentrifuge rotor, or equivalent, and centrifuged for 60 min at 40 K rpm, 4° C. The supernatant was transferred into 50 ml disposable tubes, approximately 20 ml/tube, taking care to avoid the viscous, chromosomal DNA. 50μg RNaseA/ml supernatant was added and the tubes were capped and incubated for 30 min at 37° C. An equal volume of TE-saturated phenol was added and the tubes were capped tightly, vortexed for 2 min, and centrifuged in a tabletop Sorvall T6000 or equivalent for 10 minutes at 3000 rpm. The aqueous (top) layer was transferred to new tubes. An equal volume of chloroform with 1% iso-amyl alcohol was added and the tubes were capped tightly and vortexed for 2 min. The tubes were then centrifuged for 10 min at 3,000 rpm. The aqueous (top) layer was transferred to 1 or 2 500 ml glass bottles and Na-acetate was added to 0.2M (1/10 volume of 2M Na-acetate) along with 2.5 volumes of ice-cold 100% ethanol. The tubes were chilled at −20° C. for 30-60 min. The tubes were transferred to a GSA rotor or equivalent, and centrifuged at 10,000 rpm for 30 min. The supernatants were decanted and pellets dried under vacuum. The plasmid pellets were dissolved and pooled in a total of 168 ml of 1X SSC. If a visible amount of precipitate adhered to the glass bottle, this was also dried, dissolved, and added to the plasmid pool. 156 g CsCl was added and mixed until the plasmid pellet and CsCl were dissolved. 12 ml stock Ethidium Bromide were added. The solution was distributed into eight $1\times3.5$ inches polyallomer quick-seal tubes for the Beckman 70Ti rotor, balanced, overlaid with light mineral oil to the top, and balanced again. The tubes were sealed and centrifuged at 20° C. and 40,000 rpm for a minimum of 40 hours. The plasmids were collected from the lower band (orange color fluorescene from Ethidium Bromide) using a 21 gauge needle attached to a 10 ml syringe. Plasmid from 8 gradients was pooled in 1 or 2 50 ml tubes and diluted with 1 volume of 1X SSC. An equal volume of CsCl-saturated iso-amyl alcohol was added. The tubes were vortexed and centrifuged for 5 min at 3000 rpm. The alcohol (top, pink) layer was discarded. Extraction with CsCl-saturated iso-amyl alcohol was continued until no pink color remained (approximately 3 times) and then dialyzed overnight against 4 liters of water. Plasmid was collected from the dialysis bag into 30 ml COREX (Fisher) centrifuge tubes.

Na-acetate was then added and to 0.2M along with 2.5 volumes of ice-cold 100% EtOH. The tubes were stored at −20° C. The precipitated plasmid was pelleted by centrifugation at 10,000 rpm in a Sorvall SS34 rotor for 30 min, 4° C. The supernatant was decanted and the pellet dried under vacuum. The pellet was dissolved in 14 ml TE, pH 8 and transferred to a 50 ml tube. 7 ml of TE-saturated phenol were added and followed by 7 ml chloroform with 1iso-amyl alcohol. The tube was vortexed 2 minutes and centrifuged for 10 min at 3,000 rpm. The aqueous (top) layer was transferred to a new tube and the extraction repeated. The mixture was transferred to a new tube and extracted a third time with chloroform only.

The aqueous layer was transferred to 2 30 ml Corex centrifuge tubes, Na-acetate was added to 0.2M along with 2.5 volumes of ice-cold 100% EtOH. The tubes were put into a dry ice-methanol bath for 1 hour and the precipitated plasmids pelleted by centrifugation for 30 min at 10,000 RPM. The supernatant was decanted and the pellet was dried and resuspended in approximately 2 ml sterile, distilled $H_2O$. The concentration and purity of the plasmid preparation were determined by absorbance at 260 nm and 280 nm and agarose gel electrophoresis. Generally a solution of 50μg plasmid/ml has an $OD_{260}$ of 1.0 when measured in a cuvette of 1 cm width. A high purity plasmid preparation has an $OD_{260}/OD_{280}$ ratio of approximately 2.0. Generally 3-5 mg of plasmid per 10 liters of E. coli culture were obtained. The plasmid was aliquoted and stored at −20° C. until needed. The plasmids were not stored for long periods at 4° C. or frozen and thawed repeatedly.

This procedure yielded high quality plasmid preparations suitable for transfection. Plasmid prepared in one run was plasmid.

EXAMPLE 4

Transfection of Cells

COS cells were grown in culture media (Dulbecco's Modified Eagle's Medium (DMEM) with 10% heat-inactivated fetal calf serum (FCS) and 5μg/ml Gentamicin) to 90% confluency in $150 cm^2$ tissue culture flasks. Over-confluent cells had a lower transfection efficiency. Media were aspirated and monolayers washed twice with $Ca^{30+}$ and $Mg^{++}$ deficient phosphate buffered saline (PBS-def). 2 ml of Trypsin-EDTA (0.05% trypsin and 0.53 mM EDTA in PBS-def) were added to each flask and distributed over the monolayer. Flasks were placed in a 37° C. incubator for approximately 10 minutes, until cells began to lift from the flask. 10 ml of culture media were added and the cell suspension pipetted several times to disperse cell clumps. The cell suspension was transferred to a 50 ml centrifuge tube and the cells pelleted at 2,000 rpm (approximately 800 g) for 10 min. Media was removed and cells resuspended in PBS, counted with a hemocytometer. The density was adjusted fo $2\times10^6$ cells/ml.

Three different plasmid —DEAE-dextran solutions were prepared as follows:

a 9 ml PBS
1 ml DEAE-dextran (stock at 10 mg/ml, filler sterilized)
40 μg pHIV/SeAP and 1.8 μg pHIV/TAT (in <200μl total volume)

b 9 ml PBS
1 ml DEAE-dextran
28 μg pRSV/SeAP and 1.8 μg pHIV/TAT (in <200μl total volume)

c 1.8 ml PBS
0.2 ml DEAE-dextran
8 μg pXF3 (in <40μl volume) (XF3 is the parental vector without TAT or SeAP gene sequence used for background control)
10 ml of density-adjusted cells were mixed with plasmid mix (a), 10 ml of cells mixed with (b), and 2 ml mixed with (c). The number of cells transfected was adjusted as needed. The amount of plasmid used remained at the stated concentrations per $2\times10^7$ cells The final concentration of DEAE-dextran was 0.5 mg/ml and the cell density $1\times10^6$/ml. If the number of cells in any transfection was too small there was a decrease in cells recovered with small-volume transfections.

When $2 \times 10^7$ cells were transfected, the recovery is >50%. The suspensions were incubated in a 37° C. water bath for 30 minutes. 25 ml of culture media were added to each of the two larger volume transfections, 5 ml added to the smaller volume transfection, and the suspensions were incubated for a further 30 minutes (swirling every 10 minutes). After incubation, the cells were pelleted at 2,000 rpm for 10 minutes. The supernatant was poured off and the cells resuspended in culture media. The cells were counted and the density was adjusted to $6.7 \times 10^4$ cells/ml.

150μl of cell suspension were added to each individual well of 96-well microtiter plates according to the diagram in FIG. 1A. The cultures were incubated overnight at 37° C., 5% $CO_2$, >98% humidity, before the addition of the substances to be tested. The shelves in the incubator were kept perfectly level to prevent cells from setting to the edges of the wells, resulting in uneven monolayers. The chamber was humid to prevent evaporation from the wells.

The substances to be tested were next serially diluted in microtiter plates. Stock solutions of substances in desired concentrations were made in DMSO. The final concentrations in the test plates were 1:100, 1:1,000 and 1:10,000 dilutions of the stock and 1% DMSO in media. If substances were soluble in PBS, DMSO can be omitted. The substances were first diluted in drug plates to 1:25, 1:250, and 1:2,500 in culture media with 4% DMSO. 50μl of the diluted test substance solutions were then added to each sample well which contained cells in 150μl culture media per well.

Compounds/broths were diluted and added to the test plates according to the following:
1) Diluent was added as set forth in FIG. 1B.
2) The dilution of compounds/broths was as follows:
   a) addition of stock compound/broths to wells in rows A and E was as set forth in FIG. 1C.
   b) successive 10-fold dilutions completed as set forth in FIG. 2A.
3) Compounds/broths were added to test plates as set forth in FIG. 2B.

The diluted compounds/broths in the bottom half of the drug plate were transferred similarly (e.g. the number of drug plates was half that of test plates) as set forth in FIG. 2C.

Nonspecific inhibitors, e.g. actinomycin were put into wells D9–D12 and E9–E12 as nonspecific inhibitor controls.

Figure 3A:
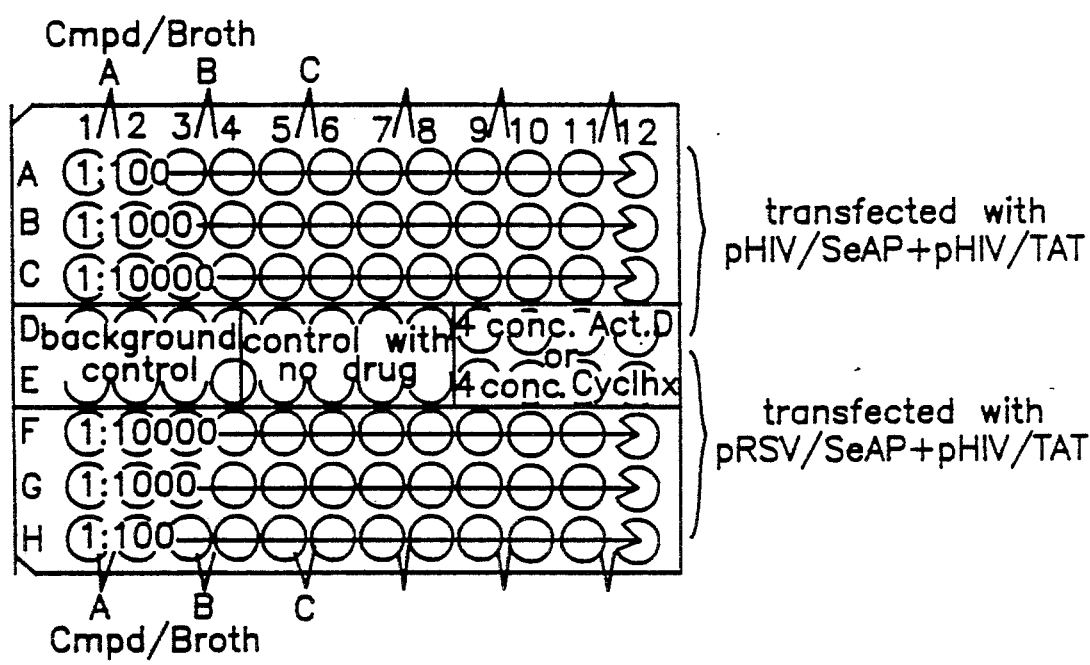
Figure 4:
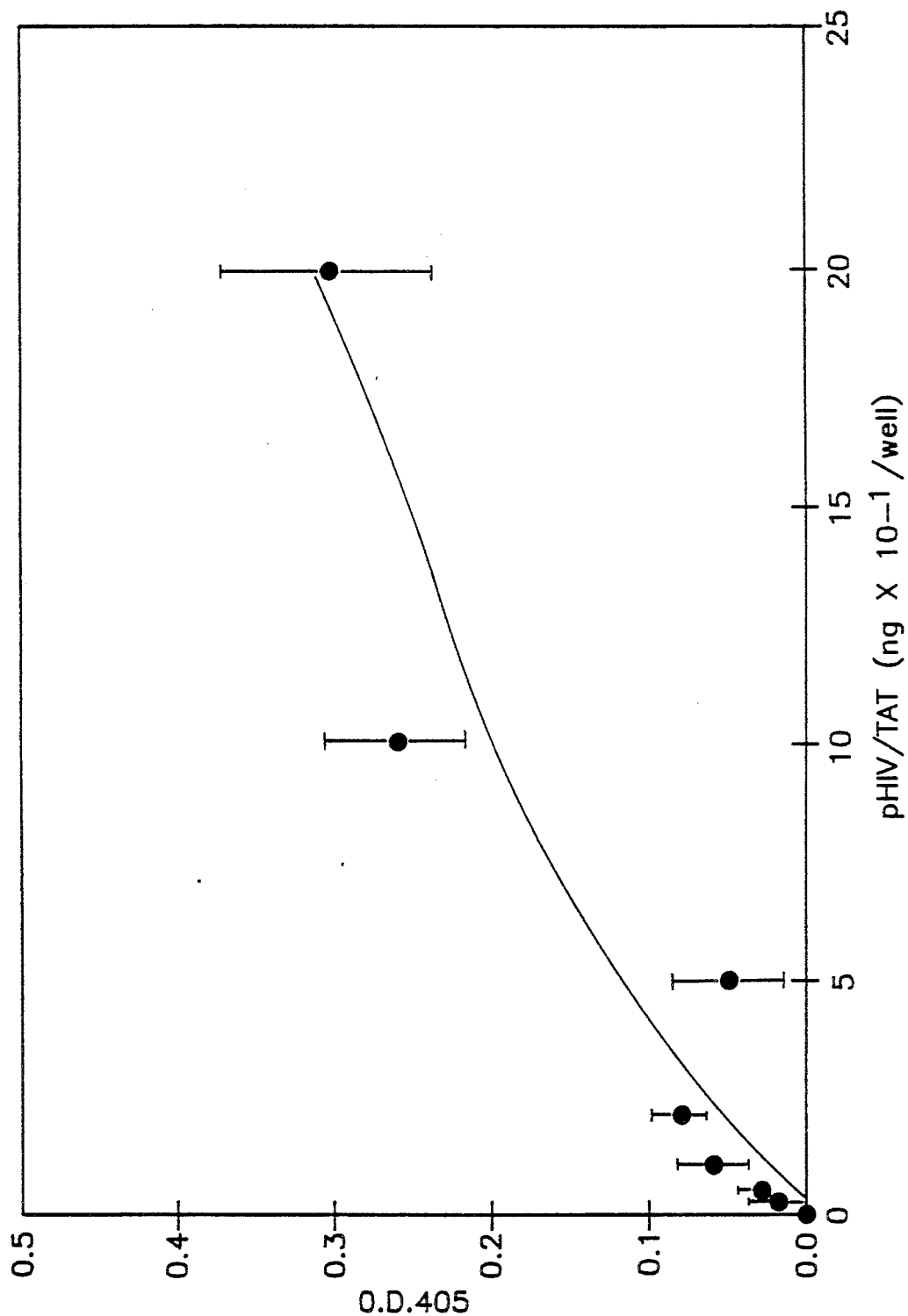
FIG. 4: Illustrates the linear relationship between TAT and SeAP production in cells co-transfected according to the method of the invention.
Figure 5:
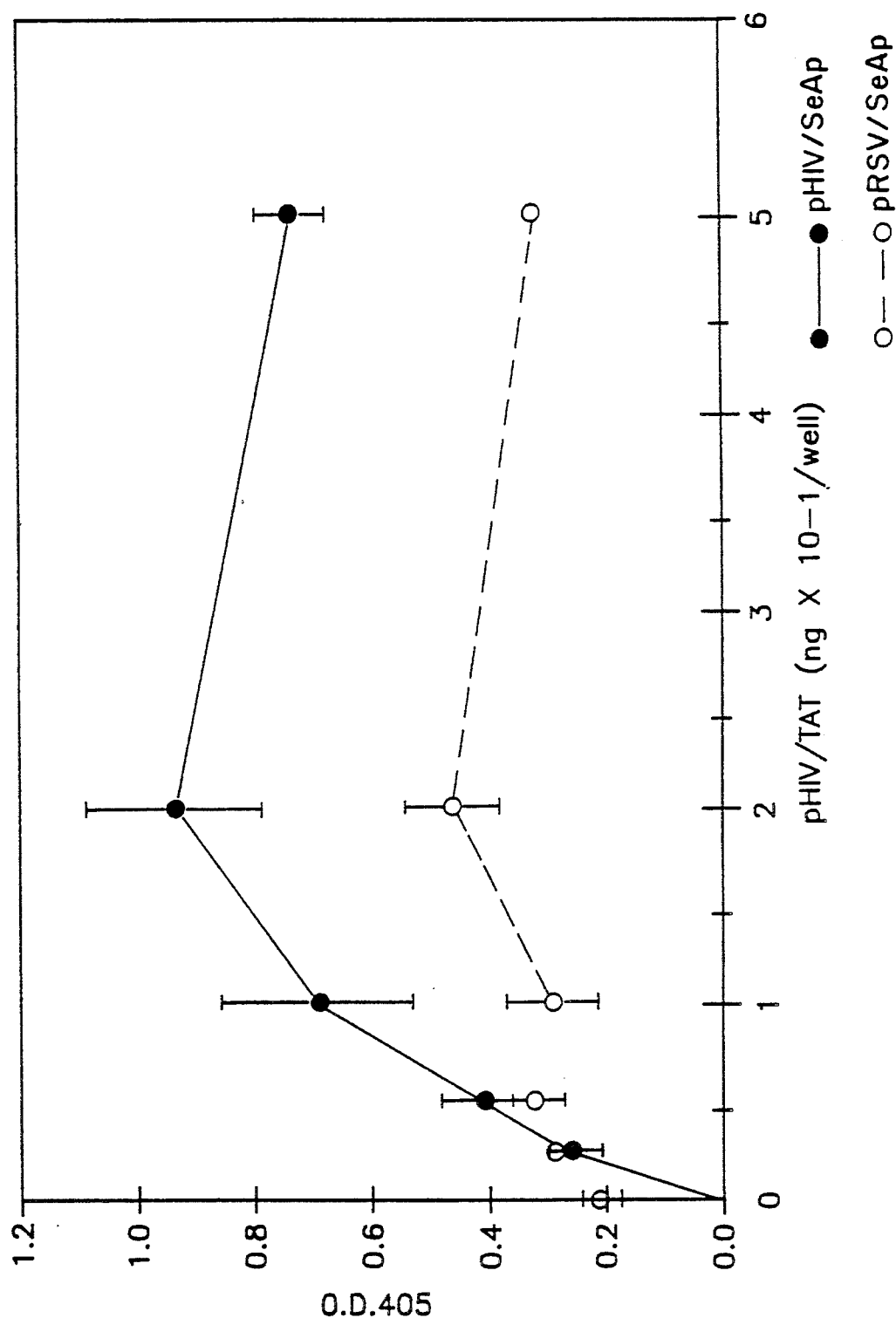
FIG. 5: Demonstrates that production of SeAP activity when the SeAP gene is driven by the HIV promoter is directly dependent on the quantity of plasmid encoding for TAT (X-axis). When SeAP is driven by the RSV promoter, SeAP activity is in dependent of the quantity of plasmid encoding TAT. Consequently, in this assay, the RSV promoter functions as a control.
Figure 6:
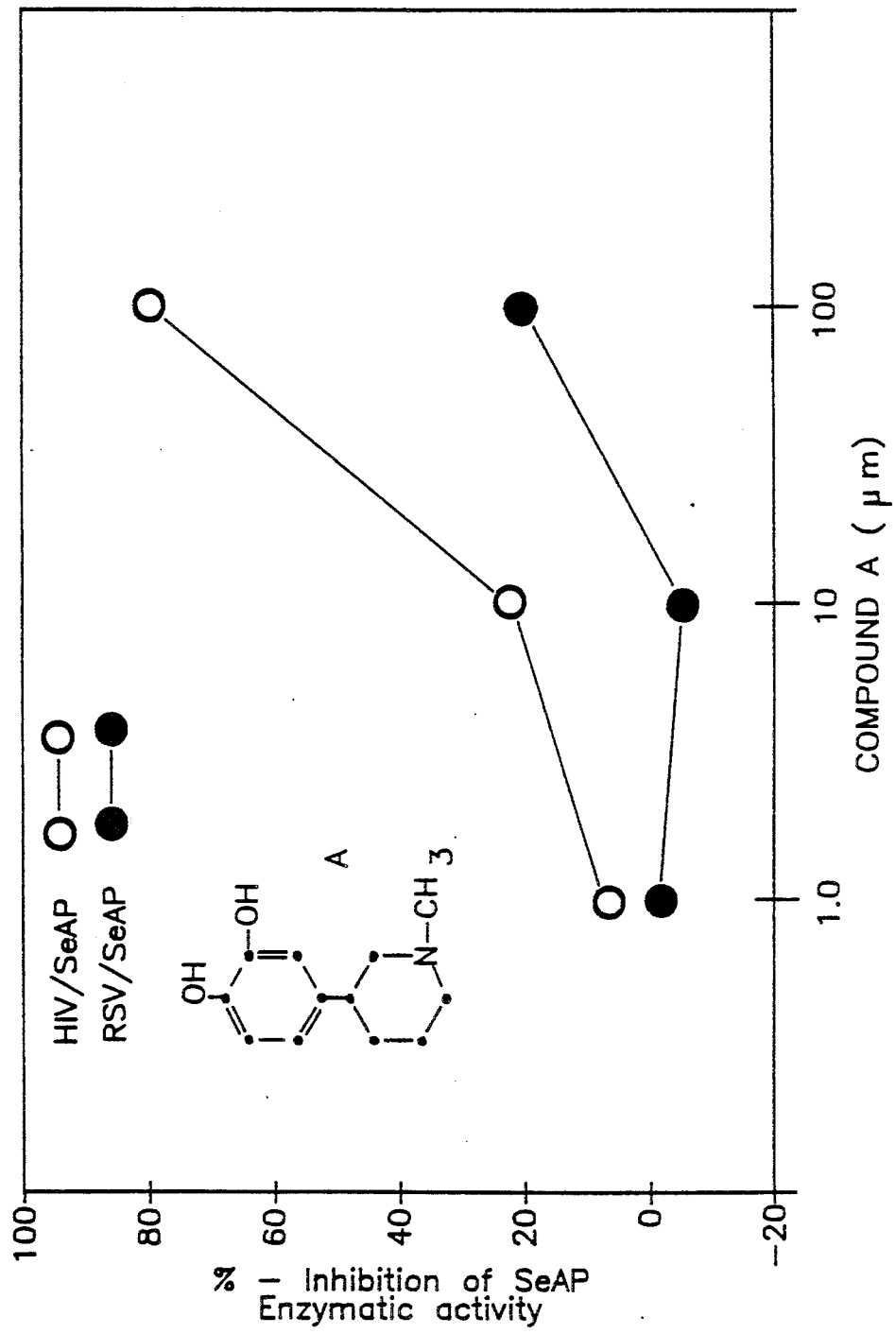
FIG. 6: Illustrates the test of a TAT inhibiting compound in the anti-TAT assay of the instant invention. The instant assay was also used to discover the anti-TAT activity of other compounds. The results are set forth in co-pending patent applications 07/428,558 and 07/428,559 filed on the same day as this application and hereby incorporated by reference.

The final layout of the test plate is shown in FIG. 3A. A symmetrical layout from the center of the plate minimized difficulties encountered due to the "edge effect". To ensure that any drug inhibition was real and not merely a reflection of the "edge effect", "no drug" plates were carried through the procedure as references for each assay.

The test plates were incubated for 48 hours (37° C., 5% $CO_2$, >98% humidity) before the culture media is tested for SeAP activity.

EXAMPLE 5

SeAP ASSAY

1) Buffer and substrate were prepared as follows:

Buffer: prepared fresh for each assay
40 ml 1M diethanolamine
0.4 ml 0.5M $MgCl_2$
4 ml 1 mM $ZnSO_4$
152 ml sterile distilled water Substrate 10 mM 2 Na-nitrophenylphosphate was prepared by dissolving
200 mg of substrate in 152 ml of buffer.
2) 60μl of 10mM substrate was added to each well of the 96 well assay plate, one assay plate for each test plate.
3) 40μl of supernatant from each well of the test plate was added to the assay plate and mixed.
4) The assay plates were incubated (with covers on) for 30 min at 37° C., in a humidified chamber.
5) After incubation, 100μl of 0.3N NaOH was added to each well to stop the reaction.
6) The plates were read at 405 nm with an ELISA plate reader.
7) Those compounds which inhibited SeAP production in the PHIV/SeAP transfected cells but not in the pRSV/SeAP transfected control cells exhibited anti-TAT activity without exhibiting non specific cytotoxicity.

The enzyme reaction in step (4) was timed for each individual microtiter Plate. Usually, 20 plates were read by an ELISA reader at a given time within two hours of completion of step 5. Prolonged standing of the assay plates increased the background reading because of spontaneous decomposition of the substrate.

EXAMPLE 6

Calculation of results

The results were calculated according to the following formula:

$$\% \text{ Inhibition} = 100 - 100 \times \frac{(\text{Ave } O.D. \text{ at each dilution}) - (\text{Ave } O.D. \text{ of Blank})}{(\text{Ave } O.D. \text{ of Control}) - (\text{Ave } O.D. \text{ of Blank})}$$

We claim:
1. A method for determining the anti-viral transactivating activity of a substance, said method comprising the steps of:
   a) contacting the test substance with a cultured first mammalian cell capable of expressing secreted Alkaline Phosphatase ("SeAP"), said cell comprising;
      a gene capable of causing the expression of SeAP by said cell, a viral transactivator-activated promoter for activating said gene which causes SeAP expression by said cell and a transactivator gene which is capable of causing the expression of a viral transactivator which activates said promoter,
      to determine if said substance inhibits the production of SeAP by said cell;
   b) contacting said substance with another cultured mammalian cell capable of expressing SeAP, said cell comprising
      a gene capable of causing the expression of SeAP by said cell and a self-activating viral promoter which activates said SeAP expression,
      to determine if said substance inhibits the production of SeAP by said second cell; and c) determining if the addition of the substance selectively inhibits the amount of SeAP produced by said first mammalian cell whereby such selective inhibition of SeAP expression by said first cell correlates to selective inhibition of viral transactivator expression and thereby demonstrates the anti-viral transactivating specific activity of the substance.

2. A method for detecting the anti-HIV-TAT activity of a substance, said method comprising the steps of:
 a) contacting the test substance with a cultured first mammalian cell capable of expressing secreted Alkaline Phosphatase ("SeAP"), said cell comprising
   a gene capable of causing the expression of SeAP by said cell and HIV-TAT gene under the control of HIV-LTR,
   to determine if said substance inhibits the production of SeAP by said cell;
 b) contacting said substance with another cultured mammalian cell capable of expressing SeAP, said cell comprising
   a gene which causes the cell to express SeAP and the Raus Sarcoma virus-LTR ("RSV-LTR") which activates said SeAP expression,
   to determine if said substance inhibits the production of SeAP by said second cell; and
 c) determining if the addition of the substance selectively inhibits the amount of SeAP produced by said first mammalian cell whereby such selective inhibition of SeAP expression correlates to selective inhibition of HIV-TAT expression and demonstrates the anti-HIV-TAT specific activity of the substance.

3. The method of claim 1 wherein the anti-viral transactivating activity is anti-TAT and the viral promoter is HIV-LTR.

4. The method of claim 3 wherein the mammalian cell is transfected with a plasmid which causes cellular production of TAT and SeAP.

5. The method of claim 4 wherein the mammalian cells are COS cells.

6. The method of claim 5 wherein the substance to be tested is a synthetic compound, microbial broth, biological preparation or biological molecule.

7. The method of claim 1 wherein the anti-viral transactivating activity is anti-X activity, and the viral promoter is the promoter of HBV core antigen.

8. The method of claim 7 wherein the mammalian cells are transfected with plasmids causing production of X and SeAP.

9. The method of claim 8 wherein the substance to be tested is a synthetic compound, microbial broth, biological preparation or biological molecule.

10. The method of claim 1 wherein the anti-viral transactivating activity is anti-ICP4 activity, and the viral promoter is HSV early or late gene promoter.

11. The method of claim 10 wherein the mammalian cells are transfected with plasmids causing production of ICP4 and SeAP 12. The method of claim 11 wherein the substance to be tested is a synthetic compound, microbial broth, biological preparation, or biological molecule.

13. The method of claim 2 wherein the mammalian cells are COS cells.

14. The method of claim 13 wherein the substance to be tested is a chemical compound.

15. The method of claim 14 wherein SeAP inhibition is measured by colorimetric assay.

* * * * *